(12) United States Patent
Babico et al.

(10) Patent No.: US 8,427,641 B2
(45) Date of Patent: Apr. 23, 2013

(54) COMPACT DETECTOR FOR SIMULTANEOUS PARTICLE SIZE AND FLUORESCENCE DETECTION

(75) Inventors: John Y. Babico, Tucson, AZ (US); Chen Liang, Tucson, AZ (US)

(73) Assignee: Azbil Biovigilant, Inc., Tucson, AZ (US)

( * ) Notice: Subject to any disclaimer, the term of this patent is extended or adjusted under 35 U.S.C. 154(b) by 332 days.

(21) Appl. No.: 12/642,705

(22) Filed: Dec. 18, 2009

(65) Prior Publication Data

US 2010/0165341 A1 Jul. 1, 2010

Related U.S. Application Data

(60) Provisional application No. 61/138,876, filed on Dec. 18, 2008.

(51) Int. Cl.
*G01N 15/02* (2006.01)
(52) U.S. Cl.
USPC .......................................... 356/336; 356/343
(58) Field of Classification Search .......... 356/335–343; 250/574
See application file for complete search history.

(56) References Cited

U.S. PATENT DOCUMENTS

| | | | |
|---|---|---|---|
| 4,251,733 A | 2/1981 | Hirleman, Jr. | |
| 4,273,443 A * | 6/1981 | Hogg | 356/343 |
| 4,351,709 A * | 9/1982 | Goetz | 204/549 |
| 4,523,841 A * | 6/1985 | Brunsting et al. | 356/73 |
| 5,089,714 A * | 2/1992 | Ludlow et al. | 250/574 |
| 5,298,968 A * | 3/1994 | Cheung | 356/338 |
| 5,436,717 A | 7/1995 | Ogino | |
| 5,467,189 A * | 11/1995 | Kreikebaum et al. | 356/336 |
| 5,484,571 A | 1/1996 | Pentoney, Jr. et al. | |
| 5,646,597 A | 7/1997 | Hamburger et al. | |
| 5,767,967 A * | 6/1998 | Yufa | 356/336 |
| 5,969,622 A | 10/1999 | Hamberger et al. | |
| 5,986,555 A | 11/1999 | Hamberger et al. | |
| 6,008,729 A | 12/1999 | Hamberger et al. | |
| 6,087,947 A | 7/2000 | Hamberger et al. | |
| 6,750,006 B2 | 6/2004 | Powers et al. | |
| 6,768,545 B2 | 7/2004 | Matsuda et al. | |
| 6,819,411 B1 * | 11/2004 | Sharpe et al. | 356/72 |
| 6,885,440 B2 | 4/2005 | Silcott et al. | |

(Continued)

FOREIGN PATENT DOCUMENTS

| | | |
|---|---|---|
| GB | 1298658 | 12/1972 |
| GB | 2193570 | 2/1988 |
| JP | 2006250685 | 9/2006 |

OTHER PUBLICATIONS

International Preliminary Report on Patentability dated Jun. 21, 2011.

(Continued)

*Primary Examiner* — Hoa Pham
(74) *Attorney, Agent, or Firm* — Quarles & Brady LLP; Michael J. Curley; Dale Regelman

(57) ABSTRACT

A particle detection and classification system is disclosed. The system determines the size of measured particles by measuring light scattered by the particles. The system simultaneously determines whether measured particles are biological or non-biological by measuring fluorescent light from the particles. The system uses a parabolic reflector, and optionally, a spherical reflector to collect fluorescence light.

20 Claims, 7 Drawing Sheets

U.S. PATENT DOCUMENTS

| | | |
|---|---|---|
| 6,936,828 B2 | 8/2005 | Saccomano |
| 7,053,783 B2 | 5/2006 | Hamberger et al. |
| 7,355,706 B2 | 4/2008 | Girvin et al. |
| 7,430,046 B2 | 9/2008 | Jiang et al. |
| 7,551,279 B2 | 6/2009 | Adams et al. |
| 2003/0223063 A1 | 12/2003 | Hill et al. |
| 2004/0159799 A1 | 8/2004 | Saccomanno |
| 2006/0232776 A1 | 10/2006 | Hairston et al. |
| 2007/0194244 A1 | 8/2007 | Adams et al. |
| 2007/0285662 A1 | 12/2007 | Sharpe et al. |
| 2008/0002180 A1 | 1/2008 | Gigioli et al. |
| 2010/0060893 A1* | 3/2010 | Norton et al. .......... 356/301 |
| 2010/0159504 A1* | 6/2010 | Babico et al. .......... 435/34 |
| 2010/0290041 A1 | 11/2010 | Graham et al. |

OTHER PUBLICATIONS

Lloyd et al., "Is What You Eat and Drink Safe? Detection and Identification of Microbial Contamination in Foods and Water," Proceedings of the IEEE, Jun. 6, 2003, pp. 908-914, vol. 91, No. 6.

European Patent Office, Extended European Search Report for European Application No. 09838010.8, Oct. 25, 2012.

\* cited by examiner

COMPACT DETECTOR FOR SIMULTANEOUS PARTICLE SIZE AND FLUORESCENCE DETECTION

CROSS-REFERENCE TO RELATED APPLICATION

This application claims priority to copending U.S. Provisional Application entitled "Simultaneous Particle Size And Fluorescence Detector," having Ser. No. 61/138,876, filed Dec. 18, 2008, the contents of which are entirely incorporated herein by reference.

FIELD OF INVENTION

The present invention relates to generally to a system for detecting airborne or waterborne particles, and more particularly to a system for detecting airborne or waterborne particles and classifying the detected particles by size and biological status. The invention has particular utility in detecting and classifying biological particles or contamination in clean environments such as aseptic manufacturing facilities, but has utility in any environment where rapid detection of biological particles is advantageous.

BACKGROUND OF INVENTION

A variety of manufacturing environments require strict control over the presence of foreign debris in the air. Semiconductor manufacturing, for example, has long required "clean-rooms" that use extensive air filtering to reduce the number and size of particles in the air to some acceptable level. Other manufacturing environments have similar but distinct requirements. For example, in pharmaceutical and medical device manufacturing environments, hospitals, and food processing or preparation environments it is critical to control not only the number of particles in the air, but minimization of biological particles is also of particular importance. Microbial contamination, for example, can render an entire batch of pharmaceutical product unusable leading to significant monetary losses in the manufacturing process. Accordingly, it is advantageous to have instantaneous detection of contamination events, including instantaneous information about whether a contamination event is biological or non-biological, during the manufacturing process for pharmaceuticals or medical devices. Such a capability is also advantageous in post offices or other government facilities, which may be targets of biological or chemical terrorist attacks.

Various detectors have been designed to detect fluid borne particles by measuring the amount and directionality of light scattered by particles in a sampling area. Some of these detectors are described in U.S. Pat. Nos. 5,646,597, 5,969,622, 5,986,555, 6008,729, 6,087,947, and 7,053,783 all to Hamburger et al, and U.S. Pat. No. 7,430,046 to Jiang et al. These detectors all involve direction of a light beam through a sample of environmental air such that part of the beam will be scattered by any particles in the air, a beam blocking device for transmitting only light scattered in a predetermined angular range corresponding to the predetermined particle size range, and a detector for detecting the transmittal light. An alarm is actuated if the light detected at the detector is above a predetermined level. Some of these detectors, for example the detectors described in U.S. Pat. No. 7,430,046 to Jiang et al., also use the measurement of fluorescence exited in measured particles by illumination with source light to classify measured particles as biological or non-biological.

Conventional particle detectors that rely on scattering or fluorescence measurement confront a common set of challenges. For example, in detectors or particle counters that are designed for detection of scattered light, the scattered light signal must be extracted from the incident illumination light source signal. This involves detecting a weak signal (scattering from small particles) from a very noisy background (glare from the laser source). Additionally, conventional particle detectors that provide simultaneous scattering and fluorescence measurements must be able to (1) detect enough of the florescent light to result in a usable signal and (2) separate out the signal generated by detected fluorescent light from other electrical or optical noise in the system.

Some of these problems are exacerbated when the particles to be measured are suspended in some fluid other than air or a gas having a low index of refraction. If the particles to be measured are suspended in water, for example, which has an index of refraction higher than air, a variety of effects can conspire to reduce the amount of scattered or fluorescent light available for measurement. Wave guiding within the fluid line, for example, can trap light being fluorescently emitted or scattered at high angles. Additionally, Fresnel reflections at the fluid-air boundary or the boundary between the fluid line and the surrounding air can further reduce the amount of light available to measure. Additionally, the corners of a fluid conduit having a rectangular cross section or the curved surface of a fluid conduit having a circular cross section can cause lensing effects and other optical aberrations that degrade the signal to noise ratios at the detectors.

SUMMARY OF THE INVENTION

The present invention relates generally to systems and methods for performing measurements of the size of particles suspended in a fluid, while simultaneously using particle fluorescence to determine whether the measured particles are biological or non-biological. Systems according to embodiments of the invention employ more efficient collection optics than conventional systems to allow collection of more light emitted by particle fluorescence.

In certain embodiments, the invention includes a particle detection and classification system. The system includes a sampling area including a fluid to be measured, a light source on a first side of the sampling area, a first detector on a second side of the sampling area, a second detector on a second side of the sampling area and a parabolic reflector having a vertex located on the first side of the sampling area and a focal point within the sampling area. The light source supplies substantially collimated light to the sampling area along a first axis, the first detector measures light scattered in the direction of the second side of the sampling area at predetermined angles, the parabolic reflector collects light emitted by illuminated particles within the sampling area by fluorescence and directs the collected light in a substantially collimated fashion in the direction of the second side of second sampling area, and the second detector measures fluorescence light collected by the parabolic reflector.

Certain embodiments include a scattered light collector lens located on the second side of the sampling area having a front focal point located within the sampling area, where scattered light traversing the scattered light collector lens is intercepted by the first detector. In other embodiments, the scattered light collector lens collimates light scattered by particles within the sampling area. Additional embodiments include a scattered light condenser lens that receives collimated light from the scattered light collector lens and focuses the collimated light onto the first detector.

Other embodiments include a beam blocking device arranged on the first axis on the second side of the sampling area, and the beam blocking device intercepts light from the light source after it emerges from the sampling area. Certain embodiments include a long-pass filter arranged on the first axis on the second side of the sampling area, where the long-pass filter selectively transmits light having a wavelength of light emitted by fluorescence by illuminated particles in the sample area. Some embodiments include a fluorescent light condenser lens located on the second side of the sampling area that receives collimated light from the parabolic reflector and directs the collimated light to the second detector.

In certain embodiments, any combination of the second detector, beam blocking device, long-pass filter and fluorescent light condenser lens are sized and/or arranged to partially block light scattered in the direction of the second side into a predetermined range of angles. In some embodiments, the light source is an LED or a diode laser, and the light source emits at a wavelength of approximately between 350 nm and 410 nm.

Certain embodiments include a spherical reflector on a second side of the sampling area, wherein the spherical reflector has a center of curvature co-incident with the focal point of the parabolic reflector. Some embodiments include a scattered light collection lens having an optical power and position such that the sampling area is imaged onto the first detector. Some embodiments include a scattered light collection lens that receives collimated light from the parabolic reflector and focuses the collimated light onto the first detector.

In some embodiments, the sampling area is defined by a fluid line carrying a fluid having an index of refraction greater than 1.0. In certain embodiments, the fluid line has a substantially rectangular cross section. In some embodiments, the spherical reflector includes a pair of optically absorptive masks arranged to intercept stray light caused by interaction between light from the light source and the corners of the fluid line. Certain embodiments include a first cylindrical lens in optical communication with the first detector and a second cylindrical lens in optical communication with the second detector.

Certain embodiments include a particle detection and classification system that includes a sampling area including a fluid to be measured, a light source on a first side of the sampling area, a first detector on a second side of the sampling area, a second detector on a second side of the sampling area, and a parabolic reflector having a vertex located on the first side of the sampling area and a focal point within the sampling area. The light source supplies substantially collimated light defining a first axis, and the light source, the sampling area, the first detector and the second detector are located along the first axis.

Certain embodiments include a spherical reflector on a second side of the sampling area, and the spherical reflector has a center of curvature co-incident with the focal point of the parabolic reflector.

Certain embodiments include a particle detection and classification system having a sampling area including a fluid to be measured, a light source on a first side of the sampling area, a first detector on a second side of the sampling area, a second detector on a second side of the sampling area, a parabolic reflector having a vertex located on the first side of the sampling area and a focal point within the sampling area, a first cylindrical lens in optical communication with the first detector and a second cylindrical lens in optical communication with the second detector. The sampling area is defined by a fluid line carrying a fluid, wherein the fluid line or the fluid has an index of refraction greater than 1.0.

Certain embodiments include a spherical reflector on a second side of the sampling area, where the spherical reflector has a center of curvature co-incident with the focal point of the parabolic reflector. In some embodiments, the spherical reflector includes a pair of optically absorptive masks arranged to intercept stray light caused by interaction between light from the light source and the edges of the fluid line.

Systems according to embodiments of the invention confer certain advantages over conventional systems and methods. For example, systems according to embodiments of the invention are better suited to measure particles suspended in liquids having higher indices of refraction than air. Additionally, systems according to embodiments of the invention make more efficient use of space and can be configured such that all light collection occurs along a single axis. This allows for particle detectors according to embodiments of the invention to be entirely contained within a single, compact cylindrical package. Additionally, by co-locating all the optics along a single axis, systems according to embodiments of the invention are easier to optically align.

BRIEF DESCRIPTION OF THE DRAWINGS

Implementations of the invention will become more apparent from the detailed description set forth below when taken in conjunction with the drawings, in which like elements bear like reference numerals.

DETAILED DESCRIPTION OF THE INVENTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow charts included are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
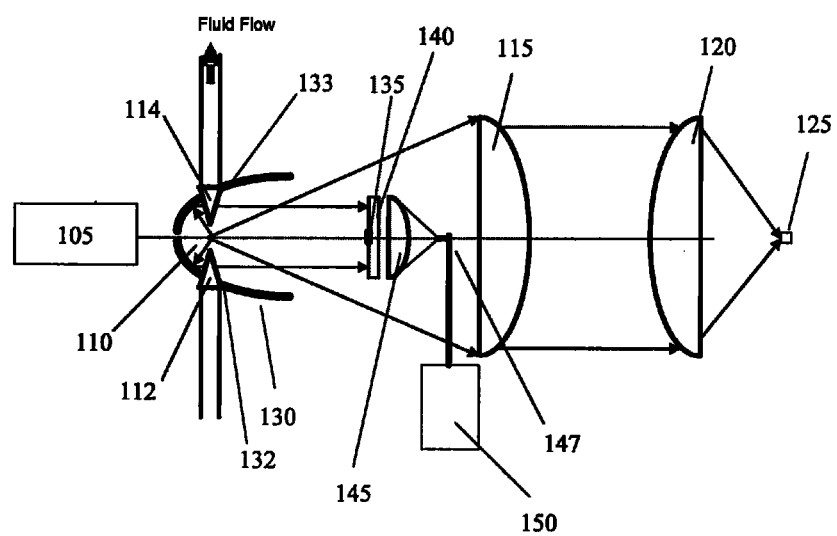
FIG. 1 is a schematic diagram of an optical system according to an embodiment of the invention for performing simultaneous fluorescence and scattering measurement using a parabolic reflector for collection of fluorescence light.

FIG. 1 shows a particle detector including a parabolic reflector for collecting light emitted by particle fluorescence according to an embodiment of the invention. The system of FIG. 1 includes a light source 105. In one embodiment, light source 105 produces an output having a wavelength between 270 nm and 410 nm. In one embodiment, light source 105 produces an output having a wavelength between 350 nm and 410 nm. In one embodiment, light source 105 produces an output having a wavelength of about 405 nm. The spectral characteristics of light source 105 are such that light emitted by light source 105 is capable of undergoing Mie scattering when interacting with particles of a size range of interest. Additionally, light source 105 is selected to have a wavelength capable of exciting intrinsic fluorescence from metabolites inside microbes and other biological particles. A wavelength of about 270 nm to 410 nm is chosen based on the observation that microbes and biological particles contain at least one of a number of primary metabolites that exhibit fluorescence: tryptophan, which normally fluoresces at excitation wavelengths of about 270 nm, with a range of about 220 nm to about 300 nm; nicotinamide adenine dinucleoetide (NADH), which normally fluoresces at excitation wavelengths of about 240 nm, with a range of about 320 nm to about 420 nm; and riboflavin, which normally fluoresces at wavelengths of about 200 nm, with a range of between 320 nm to about 420 nm. In the case of bacterial endospores, dipicolinic acid (DPA) normally fluoresces at excitation wavelengths of about 400 nm, with a range of about 320 nm to about 420 nm. A light source having a wavelength output of about 350 nm to about 410 nm ensures excitation of two of the three aforesaid primary metabolites: NADH and riboflavin, as well as DPA. Selection of this wavelength band allows for fluorescence to be generated and detected in bio-particles, but excludes excitation of non-biological sources of florescence such as diesel engine exhaust and other inert particles such as dust or baby powder.

Light source 105 can be a laser such as a diode laser, an LED or a spectrally filtered broadband source such as a lamp. Light source 105 can optionally include collimating or beam shaping optics to produce a substantially collimated output and/or an output with a substantially flat transverse power profile across the beam. Optionally, light source 105 includes an optical fiber that delivers light to the vicinity of the other elements of the system of FIG. 1. When an optical fiber is used to deliver light from a remotely situated light source, collimating or beam shaping optics may optionally be provided at the output of the optical fiber.

Light source 105 provides a substantially collimated beam of light to sampling area 110. The intersection of the substantially collimated beam from light source 110 and the sampling area creates an interrogation zone, which is an illuminated portion of the sampling area. In one embodiment, where the fluid to be measured is air or some other gas, sampling area 110 may be defined by the space between two optional gas nozzles that provide gas flow through the sampling area. In another embodiment, sampling area 110 is defined by a closed channel through which liquid to be measured flows. A closed channel or conduit can also be used to carry air, or some other gas, being measured. In one embodiment, the closed channel is defined by a rectangular glass tube. A closed channel or conduit according to a preferred embodiment has a rectangular cross-section with dimensions of 2×4 mm. In alternative embodiments, a glass tube having interior cross sectional dimensions of 3×0.3 mm is used. Although the word "glass" is used herein to describe closed channels or conduits typically, although not exclusively, used for liquid measurement, any optically transparent material may be suitable and should be deemed to be within the scope of embodiments of the invention. In addition to glass, for example, quartz, fused silica or plastic may be used in certain embodiments. Additionally, while specific embodiments using tubes having a rectangular cross section have been described, other shapes are acceptable, for example, tubes having circular cross-sections. Embodiments of the invention advantageously operate when any bar or line of material having an index of refraction greater than or equal to 1.0 exists in the sampling area, whether that bar be a closed fluid line of conduit, fluid inside a conduit, or even liquid being injected across two nozzles at relatively high pressure.

In the embodiment of FIG. 1, the system is configured to measure particles in air. Accordingly, sampling area 110 is defined by the space between two nozzles, an entrance nozzle 112, which supplies air to the sampling area under positive pressure, and an exit nozzle 114, which extracts air from the sampling area under negative pressure. Any space where particles contained in a fluid are interrogated by substantially collimated light should be viewed as a sampling area within the scope of embodiments of the invention.

Upon illumination from light source 105, particles within sampling area 110 scatter light by Mie scattering. Mie scattering generally scatters light at angles inversely proportional to particle size. Accordingly, relatively small particles will scatter light at higher angles relative to the scattering produced by relatively larger particles. In practice, scattered light emerges from sampling area 110 in a cone centered about an axis defined by the collimated beam emerging from light source 105. The amount of light scattered into various angles is used, according to certain embodiments of the invention, to determine the size of the particles scattering light.

The system of FIG. 1 further includes a scattered light collection lens 115. In one embodiment, scattered light collection lens is a plano-convex lens arranged with the plano side facing toward sampling area 110 to minimize the spherical aberration associated with collecting and collimating scattered light. Scattered light collection lens 115 collects and collimates light scattered at relatively high angles by particles in sampling area 110 by being configured and positioned such that its front focal plane is co-incident with sampling area 110.

The system of FIG. 1 further includes a scattered light condenser lens 120. Scattered light condenser lens 120 takes collimated light emerging from scattered light collection lens 115 and focuses that light onto scattered light detector 125, which generates an electrical signal in proportion to the amount of scattered light incident on detector 125.

The system of FIG. 1 further includes a parabolic reflector 130. The shape of parabolic reflector 130 is defined with respect to a vertex located on the axis defined by the beam of substantially collimated light emitted by light source 105. In one embodiment, parabolic reflector 130 includes a circular aperture at its vertex to allow for uninterrupted propagation of light from light source 105 to sampling area 110. Parabolic reflector 130 is laterally positioned (i.e., positioned from left to right along the axis defined by the collimated beam of light propagating from light source 105 to sampling area 110) such that its focal point is located within the plane of the sampling area 110. Particles undergoing florescent emission within the sampling area 110 will emit light isotropically, that is, will emit equal optical power into all angles defining a sphere. Parabolic reflector 130 is positioned such that it intercepts at least a portion of the backwardly emitted hemisphere of light emitted by florescence from particles within the sampling area. The entire backwardly emitted hemisphere cannot be intercepted because of the on-axis aperture for input of the beam from light source 105. In certain embodiments, the parabolic reflector 130 extends beyond the plane of sampling area 110 to collect some portion of light fluorescent light forwardly emitted into a forward hemisphere. In these cases, reflector 130 includes a first and second apertures 132, 133 for to give access to sampling area 110 to either or both of entrance and exit nozzles 112, 114, or the flow of fluid itself, in the case where entrance and exit nozzles 112, 114 are located outside the bowl of the parabolic reflector 130. Alternatively, where the fluid to be measured is liquid, reflector 130 includes a first and second apertures 132, 133 to allow-passage of a closed fluid line, for example, a glass tube. In alternative embodiments a closed conduit, such as a glass tube, is used to transport air or some other gas through sampling area 110. The fluorescent light collected by parabolic reflector 130 is substantially collimated and directed in a forward direction, that is, parallel to the axis defined by the collimated beam emitted from light source 105.

The system of FIG. 1 further includes beam blocking device 135. Beam blocking device 135 prevents further propagation of the collimated beam emitted by light source 105 after light emitted by light source 105 has propagated through sampling area 110. In one embodiment, beam blocking device 135 is a disk of optically absorptive material of a diameter somewhat greater than the beam diameter of the collimated beam emitted by light source 105. In certain embodiments, beam blocking device 135 is a disc of black anodized aluminum. In other embodiments, beam blocking device 135 is a small light box with an absorptive interior coating arranged to force light emitted by light source 105 and entering the light box to undergo multiple internal reflections. Alternatively, beam blocking device is a fold mirror that directs light emitted by light source 105 to a beam dump arranged at some position outside of the optical components pictured. Alternatively, beam blocking device 135 is a conical shape with an absorptive interior coating that the beam enters at the open side. Beam blocking device 135 can be any device or combination of devices that prevents further propagation of the collimated beam, or stray reflections caused by the collimated beam, emitted by light source 105 after light emitted by light source 105 has propagated through sampling area 110.

The system of FIG. 1 further includes a long-pass optical filter 140. In one embodiment, long-pass optical filter 140 is a reflective interference type filter that transmits light having a wavelength longer than a certain wavelength while reflecting light having a wavelength shorter than a certain wavelength. The spectral characteristics of filter 140 are such that light emitted by particles within the sampling area 110 by fluorescence is transmitted, while light having substantially the same wavelength as that emitted by light source 105 is reflected. Since fluorescence results in the emission of light having a longer wavelength than the excitation wavelength, filter 140 passes only light emitted by fluorescence, while reflecting noise (e.g., stray reflections) from the light source 105 as well as light scattered by particles within the sampling area 110 at low angles. Placing the long-pass filter 140 in the collimated beam generated by parabolic reflector 130 allows all rays to be filtered to intersect filter 140 at normal incidence. This is advantageous as the performance of interference filters tends to degrade at high angles of incidence. In one embodiment, beam blocking device 135 is attached to filter 140.

The system of FIG. 1 further includes fluorescent light condenser lens 145, which focuses the collimated beam of fluorescent light generated by parabolic reflector 130 onto the end of optical fiber 147. Optical fiber 147 transmits the focused fluorescence light to a photomultiplier tube ("PMT") 150, which generates a signal proportional to the amount of fluorescence light collected by the system.

In order to maximize the amount of fluorescence light detected, the dimensions of parabolic reflector 130 are chosen such that the collimated beam of fluorescence light generated by parabolic reflector overfills long-pass filter 140 and fluorescent light condenser lens 145. This raises the possibility that fluorescence light will find its way, in the form of optical noise, to the scattering detector 125. This potential problem is addressed, in certain embodiments, by the incorporation of additional spectral filtering optics. In certain embodiments, additional non-illustrated spectral filtering optics, for example, a short-pass filter not shown, are incorporated in the optical path of scattering detector 125 to ensure that scattering detector 125 only detects light having the same wavelength as the light source 105.

The components of the system of FIG. 1 are arranged such that only a specific range of angles of scattered light are detected by scattered light detector. This can be accomplished in a number of ways. For example, the fluorescence light collection components can be sized in such a way as to block scattered light emerging from scattering area 110 at low scattering angles. When this occurs, only light scattered at a high enough angle to miss the fluorescence light collection components, but at a low enough angle to intercept scattered light condenser lens 120 will be transmitted to scattering detector 125. Additionally, or alternatively, annular masks of optical non-transmissive material may be placed in the scattered light detection path, for example, on scattered light condenser lens 120.

Figure 2:
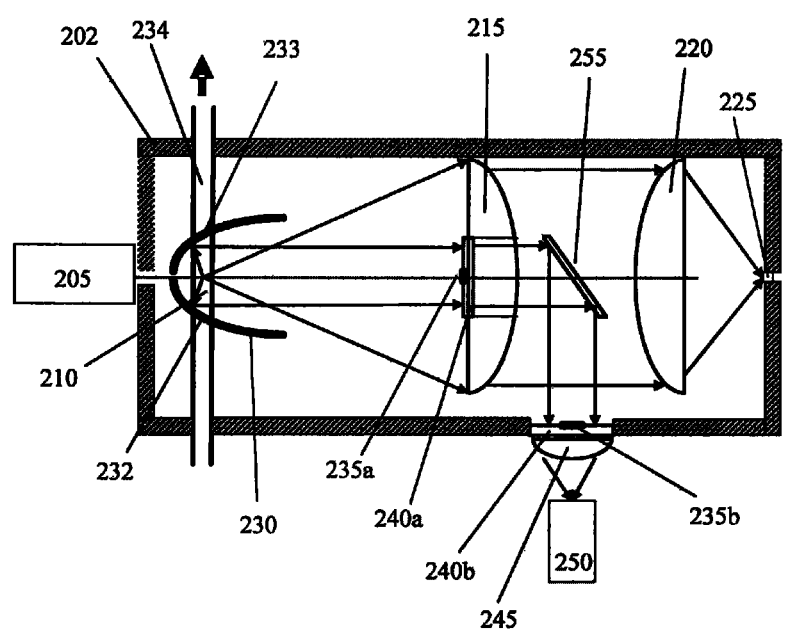
FIG. 2 is a schematic diagram of an alternate optical system according to an embodiment of the invention for performing simultaneous fluorescence and scattering measurement using a parabolic reflector for collection of fluorescence light and a fold-mirror.

While the system of FIG. 1 routes fluorescence light to a PMT by way of an optical fiber, this is not a requirement. FIG. 2 shows an alternative embodiment of the invention that uses a fold-mirror to direct fluorescence light to a PMT, which is located in an off-axis position. In the embodiment of FIG. 2, a light source 205 interrogates a sampling area 210 with a beam of substantially collimated light through a housing 202. The spectral characteristics of light source 205 are selected according to the requirements set forth above with respect to FIG. 1. As in the system of FIG. 1, particles in the sampling area 210 scatter light, which is collected by scattered light collection lens 215. A collimated beam of collected scattered light is directed to a scattered light condenser lens 220, not shown, which focuses the scattered light signal onto a scattered light detector 225.

As in the system of FIG. 1, light resulting from fluorescence by illuminated particles in the sampling area 210 is collected by parabolic reflector 230. As in the system of FIG. 1, parabolic reflector 230 includes an aperture at its vertex to admit light from light source 205, as well as apertures 232, 233 to provide a flow path for fluid to and from sampling area 210. In the example of FIG. 2, fluid to be measured is being carried by closed conduit 234 which is, for example, a glass tube. The focal point of parabolic reflector 230 is positioned in the plane of the sampling area 210 such that light emitted by fluorescence from illuminated particles within sampling area 210 is collected and collimated by parabolic reflector 230.

In one embodiment, the system of FIG. 2 includes a beam blocking device 235a and a long-pass filter 240a arranged along an axis defined by the path of the collimated beam emitted by light source 205. Beam blocking device 235a and a long-pass filter 240a serve the same functions described above with respect to FIG. 1. In one embodiment, the system of FIG. 2 further includes a fold mirror 255, which reflects the collimated beam of fluorescence light generated by parabolic reflector 230 90 degrees from its original path of travel along the axis defined by the path of the collimated beam emitted by light source 205. After reflection, the collimated beam of fluorescence light generated by parabolic reflector 230 is focused onto the input port to a PMT 250 after being focused by fluorescent light condenser lens 245.

In an alternate embodiment, beam blocking device 235b and long-pass filter 240b are located proximate to fluorescent light condenser lens 245, rather than on the primary optical axis of the system. In additional embodiments both beam blocking device 235a and beam blocking device 235b are used simultaneously to reduce optical noise in the system. In additional embodiments, long-pass filters 240a and 240b are used simultaneously to reduce optical noise in the system.

As in FIG. 1, the components of the system of FIG. 2 are arranged such that only a specific range of angles of scattered light are detected by scattered light detector. This can be accomplished in a number of ways. For example, the fluorescence light collection components can be sized in such a way as to block scattered light emerging from scattering area 210 at low scattering angles. When this occurs, only light scattered at a high enough angle to miss the fluorescence light collection components, but at a low enough angle to intercept scattered light condenser lens 220 will be transmitted to scattering detector 225. Additionally, or alternatively, annular masks of optical non-transmissive material may be placed in the scattered light detection path, for example, on the non-illustrated scattered light condenser lens.

An advantageous feature of the system of FIG. 2 is that beam blocking and spectral filtering components, e.g. elements 235a and 240a can be located inside an aperture fabricated in scattered light collection lens 215. This allows for a more compact overall housing 202, and the easier alignment of the optical components.

Figure 3:
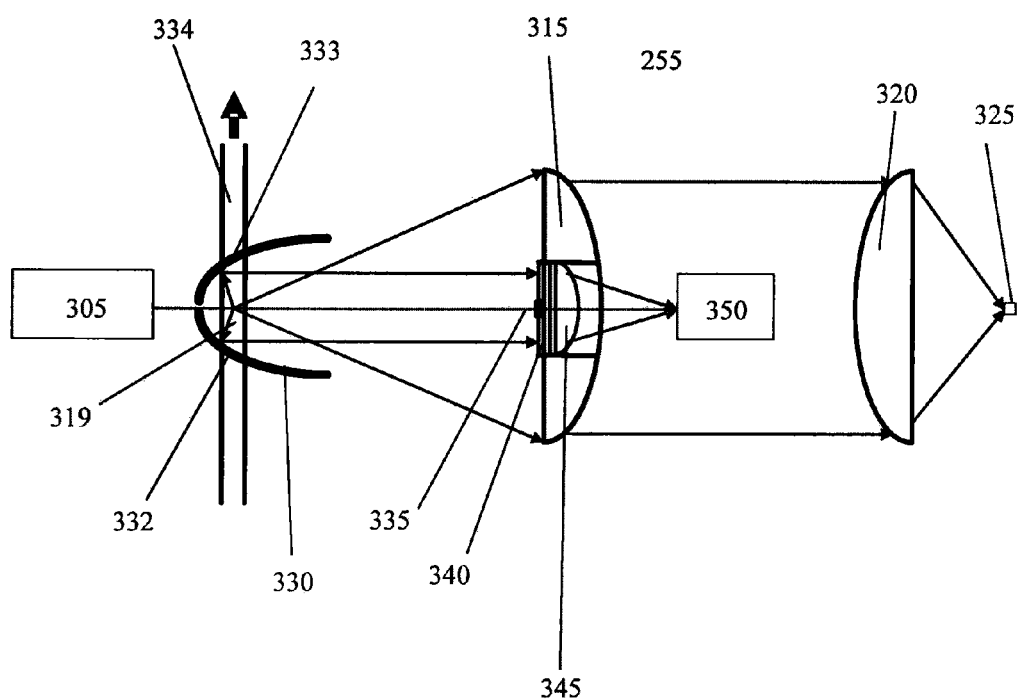
FIG. 3 is a schematic diagram of an optical system according to an embodiment of the invention for performing fluorescence measurement having all of the optical components are co-located on the same axis.

While the systems of FIGS. 1 and 2 locate the PMT (i.e., the fluorescence detector) off the primary optical axis of the system (i.e., the optical axis defined by the collimated beam generated by the light source), this is not a requirement. FIG. 3 shows a fluorescence detection system according to the invention where all components, including the PMT, are located on the same optical axis.

In the embodiment of FIG. 3, a light source 305 interrogates a sampling area 310 with a beam of substantially collimated light. The spectral characteristics of light source 305 are selected according to the requirements set forth above with respect to FIG. 1. As in the system of FIG. 1, particles in the sampling area 310 scattered light, which is collected by scattered light collection lens 315. The collimated beam of collected scattered light is directed to downstream scattered light measuring components, e.g., a condenser lens 320, a photo diode 325, and various spectral filters, which are not shown.

As in the system of FIGS. 1 and 2, light resulting from fluorescence by illuminated particles in the sampling area 310 is collected by parabolic reflector 330. As in the system of FIGS. 1 and 2, parabolic reflector 330 includes an aperture at its vertex to admit light from light source 305, as will as apertures 332, 333 to provide a flow path for fluid to and from sampling area 310. As in FIG. 2, the flow path in the embodiment of FIG. 3 is provided by glass tube 334. The focal point of parabolic reflector 330 is positioned in the plane of the sampling area 310 such that light emitted by fluorescence from illuminated particles within sampling area 310 is collected and collimated by parabolic reflector 330.

As in the system of FIG. 1, the system of FIG. 3 includes a beam blocking device 335 and a long-pass filter 340 arranged along an axis defined by the path of the collimated beam emitted by light source 305. Beam blocking device 335 and a long-pass filter 340 serve the same functions described above with respect to FIG. 1. The system of FIG. 3 further includes a fluorescent light condenser lens 345, which focuses fluorescent light onto the input port of a PMT 350. In the system of FIG. 3, the fluorescent light condenser lens 345 and the PMT 350 are arranged along the axis defined by the path of the collimated beam emitted by light source 305.

As in FIG. 1, the components of the system of FIG. 3 are arranged such that only a specific range of angles of scattered light are detected by scattered light detector. This can be accomplished in a number of ways. For example, the fluorescence light collection components can be sized in such a way as to block scattered light emerging from sampling area 310 at low scattering angles. When this occurs, only light scattered at a high enough angle to miss the fluorescence light collection components, but at a low enough angle to intercept scattered light collector lens 315 will be transmitted to scattering detector 325. Additionally, or alternatively, annular masks of optical non-transmissive material may be placed in the scattered light detection path, for example, on scattered light condenser lens.

An advantageous feature of the system of FIG. 3 is that beam blocking and spectral filtering components, e.g. elements 335 and 340 can be located inside an aperture fabricated in scattered light collection lens 315. Additionally, fluorescent light condenser lens 345 can also be located in this aperture. This allows for a more compact overall housing design, and the easier alignment of the optical components.

Figure 4:
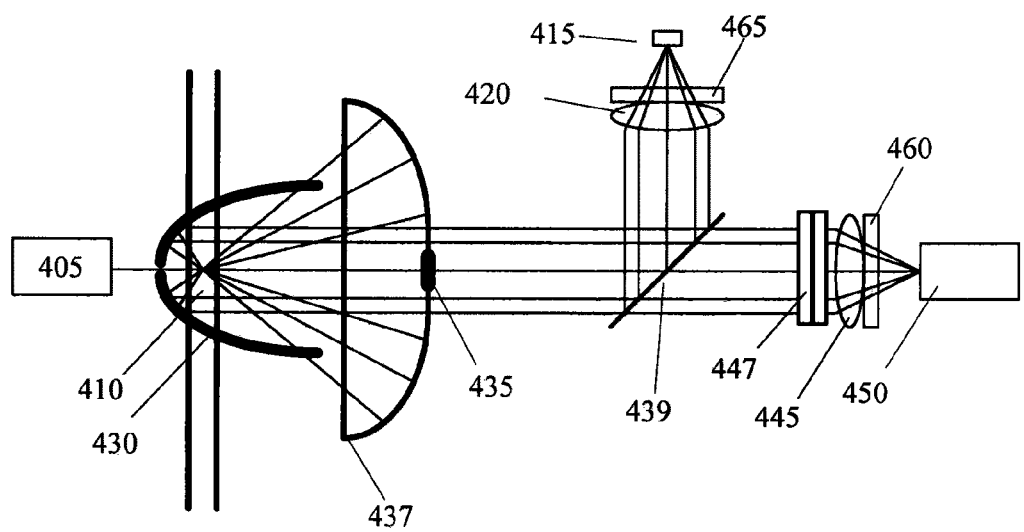
FIG. 4 is a schematic diagram of an alternate optical system according to an embodiment of the invention for performing simultaneous fluorescence and scattering measurement using a parabolic and spherical reflector for collection of light.

FIG. 4 shows an alternative embodiment of a system according to the invention having improved collection of fluorescence light. Like the systems set forth above, the system of FIG. 4 includes a light source 405, which interrogates a sampling area 410 with a beam of substantially collimated light. The spectral characteristics of light source 405 are selected according to the requirements set forth above with respect to FIG. 1. As in the system of FIG. 1, particles in the sampling area 410 scatter light in the forward direction into a scattering cone, and biological particles within sampling area 410 isotropically emit fluorescence light. In the embodiment of FIG. 4, sampling area 410 is defined by a glass tube containing a fluid containing particles to be measured. Although a fluid line, in this case a fused silica glass tube, is shown with respect to FIG. 4, this is not a requirement. The collection components of FIG. 4 work just as well when the fluid to be measured is air.

The system of FIG. 4 includes a parabolic reflector 430, which collects fluorescence light. Parabolic reflector 430 includes an aperture at its vertex to admit light from light source 405. The focal point of parabolic reflector 430 is positioned in the plane of the sampling area 410 such that light emitted by fluorescence from illuminated particles within sampling area 410 is collected and collimated by parabolic reflector 430. Unlike previously set forth embodiments, parabolic reflector 430 is limited in its extent such that it only collects light traveling in a backwards direction from sampling area 410, i.e., a direction opposite the direction of propagation of the beam of collimated light supplied by light source 405 to the sampling area 410. Because of its limited extent, parabolic reflector 430 does not interfere with the flow path that supplies fluid to be measured to sampling area 410. In alternative embodiments, parabolic reflector 430 extends beyond the plane of the sampling area 410. In these cases, parabolic reflector 430 includes apertures to allow the fluid line to pass through.

The system of FIG. 4 further includes a spherical reflector 437. Spherical reflector 437 is arranged such that its center of curvature is located in the plane of the sampling area 410 and is coincident with the focal point of parabolic reflector 430. Spherical reflector 437 redirects light emitted by fluorescence in a forward direction back to the sampling area, and therefore, back to the focal point of parabolic reflector 430, where such light is collected and collimated by parabolic reflector 430. Additionally, spherical reflector 437 redirects a portion of the light scattered in the forward direction back to the sampling area, and therefore back to the focal point of parabolic reflector 430, where such light is collected and collimated by parabolic reflector 430. Spherical reflector 437 includes an axial aperture that allows the collimated beam of fluorescence and scattered light directed by parabolic reflector 430 to pass unhindered to the right-hand side of the figure along the axis defined by the collimated beam supplied to sampling area 410 by light source 405.

The system of FIG. 4 further includes a beam blocking device 435, which is arranged to block the collimated beam supplied to the sampling area 410 by light source 405. Beam blocking device 435 is, in one embodiment, a disk of optically absorptive material, but as is set forth above with respect to FIG. 1, this is not a requirement.

The system of FIG. 4 further includes a dichroic beamsplitter 439. Dichroic beamsplitter 439 is positioned in the path of the collimated beam of fluorescence and scattered light and is configured to transmit light having a wavelength of the fluorescence light while reflecting scattered light, which has a shorter wavelength. After passing through dichroic beamsplitter 439, the beam of collimated fluorescence light encounters a pair 447 of back-to-back long-pass filters. After additional filtering by filter pair 447, the beam is focused onto the input port of a PMT 450 by a fluorescent light condenser lens 445. As in the systems described above, PMT 450 produces an electrical signal output proportionate to the amount of florescence light gathered and detected by the system.

In the system of FIG. 4, light having a wavelength shorter than the wavelength of light emitted by fluorescence is reflected by dichroic beamsplitter 439. This reflected light includes light scattered in the forward direction by particles in sampling area 410. Scattered light is brought to focus on scattered light detector 415 after being focused by scattered light condenser lens 420. In the embodiment of FIG. 4, as in previously set forth embodiments, scattered light detector 415 is a photo diode.

The components of the system of FIG. 4 are arranged such that only a specific range of angles of scattered light are detected by scattered light detector. This can be accomplished in a number of ways. For example, the axial aperture of spherical reflector 437 inherently limits the upper range of angles transmitted from sampling area 410. The diameter of the axial aperture of spherical reflector 427 can be chosen to place a limit on the high range of scatter angles. Similarly, beam blocking device 435 inherently limits the lower angular range of light transmitted from sampling area 410. Although the primary purpose of beam blocking device 435 is to block light directly from light source 405, it can be increased in diameter to block low-angle scattered light as well. Additionally, or alternatively, annular masks of optical non-transmissive material may be placed in the scattered light detection path, for example, on scattered light condenser lens 420.

Although the arrangement of FIG. 4 places the fluorescence detector on the main optical axis of the system, this is not a requirement. Depending on the design of dichroic beamsplitter 439, the positions of PMT 450 and scattered light detector 415 could be swapped.

The glass tube that defines sampling area 410 in the embodiment of FIG. 4 creates certain challenges that are not extant when the fluid to be measured is air. The glass tube runs transverse to the image plane for both the scattering light and fluorescence light collection optical systems. Accordingly, the glass tube introduces astigmatism to the images formed at the photo diode 415 and the PMT 450. This effect is exacerbated when the glass tube carries a liquid having an index of refraction greater than air. To deal with this problem, certain embodiments use a first cylindrical lens 460 and a second cylindrical lens 465 between the condenser lenses for the photo diode 415 and the PMT 450. Cylindrical lenses 460, 465 help to correct the astigmatism introduced by the glass tube in the sampling area 410.

Figure 5:
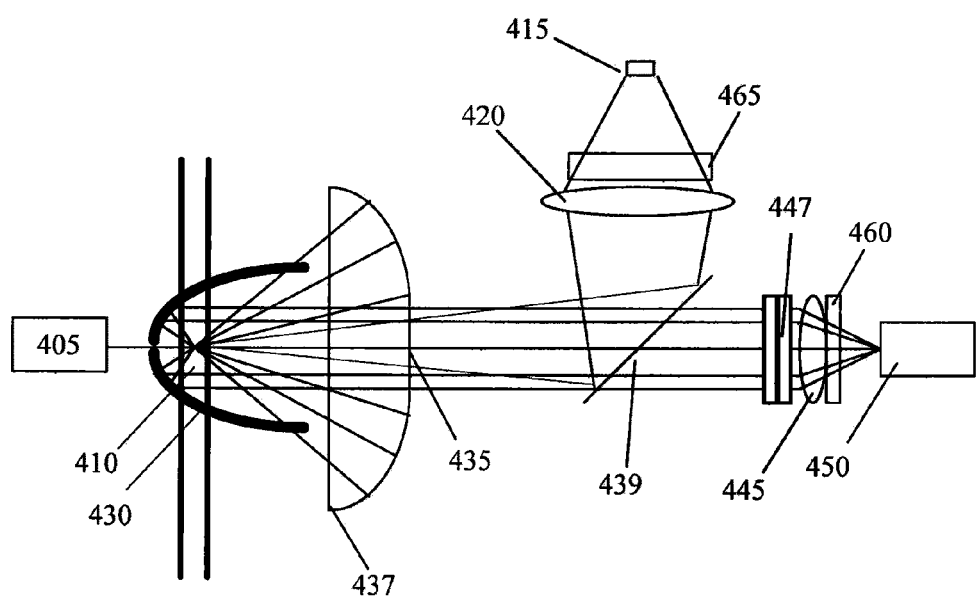
FIG. 5 is a schematic diagram of an optical system according to an embodiment of the invention for performing fluorescence measurement using both a parabolic and a spherical reflector for collection of fluorescence light.

FIG. 5 shows an alternative embodiment of the system of FIG. 4 with the scattered light detector 415 operating at finite conjugates with the plane of the sampling area 410. In the system of FIG. 5, the optical power and position of scattered light condenser lens 420 is adjusted such that it is operating at finite conjugates between scattered light detector 415 and sampling area 410. In other words, scattered light condenser lens 420 directly images the plane of sampling area 410 onto the plane of scattered light detector 415 without the assistance of intervening optics in the optical path, for example, the spherical or parabolic reflectors. This has the effect of selecting a smaller angular range of scattering light for detection, since only light that is scattered below the angle of the central aperture of the spherical reflector 437 is strongly collected by scattered light condenser lens 420.

Figure 6:
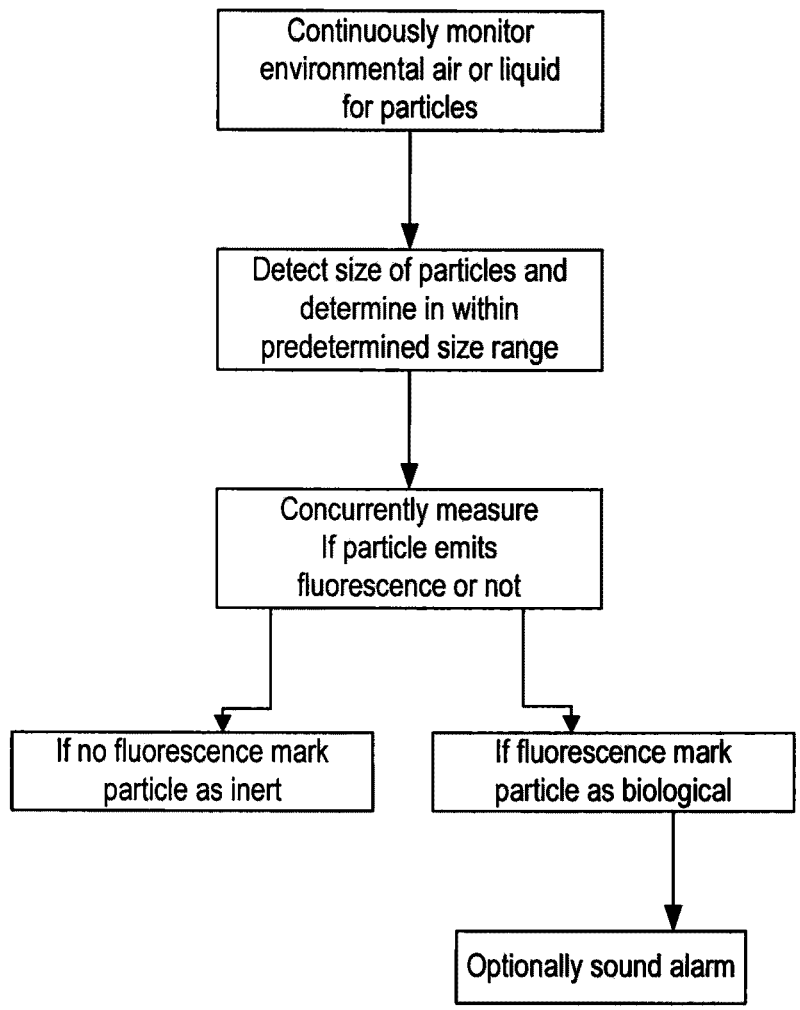
FIG. 6 is a schematic flow diagram showing method steps for performing simultaneous fluorescence and scattering measurements according to an embodiment of the invention.

FIG. 6 illustrates the steps of a method of simultaneous particle sizing and fluorescence detection according to an embodiment of the invention. The principle of operation is as follows: an instrument continuously monitors the environmental air, a gas (or liquid) to measure the size of each individual airborne particle in real time and to concurrently determine whether that particle emits fluorescence or not. One or more thresholds are set for the fluorescence signal. If the fluorescence signal falls outside set parameters, the particle is classified as inert. The fluorescence signal thresholds include one or more parameters selected from fluorescence signal intensity, fluorescence intensity as a function of particle cross-sectional area or a function of particle volume. If the fluorescence signal threshold exceeds or falls within one or more set threshold levels, the particle is marked biological. The combined data of particle size and fluorescence signal strength will determine the presence or absence of microbes on a particle-by-particle basis. Other features and considerations for fluorescence signal thresholds are disclosed in commonly owned U.S. patent application Ser. No. 12/268,366 to Morrell et al., the disclosure of which that are not inconsistent with the disclosure herein is incorporated herein by reference.

As was set forth above with respect to FIGS. 4 and 5, using a placing a closed conduit, for example a glass tube, in the sampling area presents certain challenges. In addition to the aforementioned astigmatism, a closed conduit immediately downstream from a light source may disadvantageously create back reflections a surface of the conduit into the light source. Where the light source is a laser, this can cause temporal instability. To address this challenge, certain embodiments include an anti-reflection on at least any surface of the conduit facing the light source. The downstream surface, which is the exit surface, of the conduit may also be anti-reflective coated, in certain embodiments, to enhance throughput and signal to noise ratio. Additionally or alternatively, a flat surface of the conduit can be inclined with respect to the axis defined by the beam from the light source to dump spurious retro-reflections off to the side.

Additionally, in the event that the beam from the light source overfills the conduit, disadvantageous scattering, refraction and reflection can occur at sharp edges and/or corners of the conduit. This is particularly troublesome in embodiments that use rectangular conduits to carry fluid to be tested. Embodiments according to the invention minimize these edge effects by placing a mask or aperture on the upstream surface of the conduit, i.e., the surface facing the light source, to ensure that the corners of the conduit are not illuminated. In certain embodiments, this mask or aperture is deposited in the same chemical vapor deposition process used to lay down an anti-reflective coating on the upstream surface of the conduit.

Figure 7:
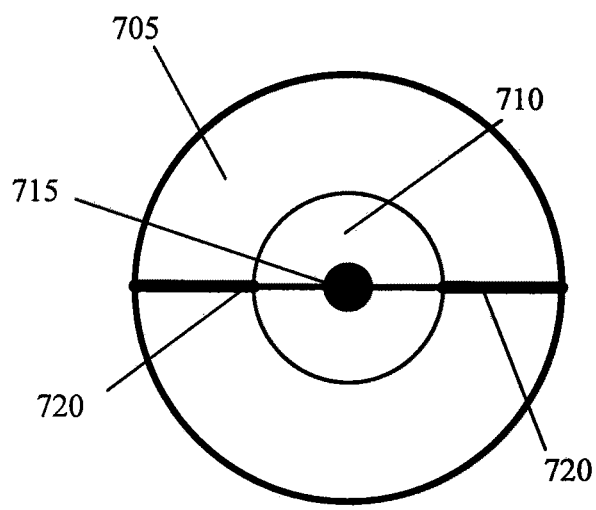
FIG. 7 is a plan view of a spherical reflector according to an embodiment of the invention.

FIG. 7 shows a plan or axial view of a spherical reflector used in systems according to embodiments of the invention, for example, systems described above with respect to FIGS. 4 and 5. The view of FIG. 7 is looking down the optical axis of the beam emitted by the light source described with respect to FIGS. 4 and 5. FIG. 7 shows a spherical reflector 705 that includes a central aperture 710. Spherical reflector 705 includes a pair of transverse mask sections 720. Mask sections 720 lie in a plane that is orthogonal to the long dimension of the conduit carrying fluid under test, i.e., the glass tube shown in FIGS. 4 and 5. From the perspective of FIGS. 4 and 5, mask sections 720 lie in a plane that is orthogonal to the plane of FIGS. 4 and 5 and includes the optical axis defined by the beam generated by the light source. As is set forth above, when the beam emitted by the light source encounters corners in the conduit, or undergoes multiple reflections off the interior walls of the conduit, it has been observed that a fan of stray light is generated downstream of the conduit. This fan is planar, being generally confined to the plane that contains the beam and the four corners of the conduit. Mask sections 720 are placed to absorb and/or prevent the back reflection of this fan of stray light off of spherical reflector 705 where otherwise it would propagate through the system.

While the preferred embodiments of the present invention have been illustrated in detail, it should be apparent that modifications and adaptations to those embodiments may occur to one skilled in the art without departing from the scope of the present invention as set forth in the following claims.

What is claimed is:

1. A particle detection and classification system comprising:
   a sampling area including a fluid to be measured;
   a light source on a first side of said sampling area;
   a first detector on a second side of said sampling area;
   a second detector on a second side of said sampling area;
   a parabolic reflector having a vertex located on the first side of said sampling area and a focal point within said sampling area;
   wherein, said light source supplies substantially collimated light to said sampling area along a first axis, said first detector measures light scattered in the direction of the second side of said sampling area at predetermined angles, said parabolic reflector collects light emitted by illuminated particles within the sampling area by fluorescence and directs said collected light in a substantially collimated fashion in the direction of the second side of second sampling area, and said second detector measures fluorescence light collected by said parabolic reflector; and
   wherein said system further comprises a spherical reflector on a second side of said sampling area, wherein said spherical reflector has a center of curvature co-incident with said focal point of said parabolic reflector.

2. The system of claim 1, further comprising a scattered light collector lens located on the second side of said sampling area having a front focal point located within said sampling area, wherein scattered light traversing said scattered light collector lens is intercepted by said first detector.

3. The system of claim 2, wherein said spherical reflector defines an axial aperture, and wherein light emitted by illuminated particles within the sampling area by fluorescence that is collected by the parabolic reflector and directed in a substantially collimated fashion in the direction of the second side of second sampling area passes through said axial aperture.

4. The system of claim 1, further comprising a beam blocking device arranged on said first axis on said second side of said sampling area, wherein said beam blocking device intercepts light from said light source after it emerges from said sampling area.

5. The system of claim 4, further comprising a long-pass filter arranged on said first axis on said second side of said sampling area, wherein long-pass filter selectively transmits light having a wavelength of light emitted by fluorescence by illuminated particles in said sample area.

6. The system of claim 5, further comprising a fluorescent light condenser lens located on the second side of said sampling area that receives collimated light from said parabolic reflector and directs said collimated light to said second detector.

7. The system of claim 6 wherein any combination of said second detector, beam blocking device, long-pass filter and fluorescent light condenser lens are sized and/or arranged to partially block light scattered in the direction of the second side into a predetermined range of angles.

8. The system of claim 1, wherein said light source comprises an LED or a diode laser, and wherein said light source emits at a wavelength of approximately between 350 nm and 410 nm.

9. The system of claim 1, further comprising a scattered light collection lens having an optical power and position such that the sampling area is imaged onto said first detector.

10. The system of claim 1, further comprising a scattered light collection lens that receives collimated light from said parabolic reflector and focuses said collimated light onto said first detector.

11. The system of claim 1, wherein said sampling area is defined by a fluid line carrying a fluid having an index of refraction greater than 1.0.

12. The system of claim 11, wherein said fluid line has a substantially rectangular cross section.

13. The system of claim 12, wherein said spherical reflector includes a pair of optically absorptive masks arranged to intercept stray light caused by interaction between light from said light source and the corners of said fluid line.

14. The system of claim 11, further comprising a first cylindrical lens in optical communication with said first detector and a second cylindrical lens in optical communication with said second detector, wherein both cylindrical lenses are configured to correct astigmatism introduced by said fluid line.

15. A particle detection and classification system comprising:
   a sampling area including a fluid to be measured;
   a light source on a first side of said sampling area;
   a first detector on a second side of said sampling area;
   a second detector on a second side of said sampling area;
   a parabolic reflector having a vertex located on the first side of said sampling area and a focal point within said sampling area; and
   a spherical reflector on a second side of said sampling area, wherein said spherical reflector has a center of curvature co-incident with said focal point of said parabolic reflector;
   wherein, said light source supplies substantially collimated light defining a first axis.

16. The system of claim 15, wherein said light source, said sampling area, and said first detector are located along said first axis, and wherein said second detector is located along a second axis orthogonal to said first axis.

17. The system of claim 15, wherein said light source, said sampling area, said first detector and said second detector are located along said first axis.

18. A particle detection and classification system comprising:
   a sampling area including a fluid to be measured;
   a light source on a first side of said sampling area;
   a first detector on a second side of said sampling area;
   a second detector on a second side of said sampling area;
   a parabolic reflector having a vertex located on the first side of said sampling area and a focal point within said sampling area;
   a first cylindrical lens in optical communication with said first detector and a second cylindrical lens in optical communication with said second detector;
   a spherical reflector on a second side of said sampling area, wherein said spherical reflector has a center of curvature co-incident with said focal point of said parabolic reflector;
   wherein, said sampling area is defined by a fluid line carrying a fluid, wherein said fluid line or said fluid has an index of refraction greater than 1.0;
   and wherein both cylindrical lenses are configured to correct astigmatism introduced by said fluid line.

19. The system of claim 18, wherein said spherical reflector includes a pair of optically absorptive masks arranged to intercept stray light caused by interaction between light from said light source and the edges of said fluid line.

20. A particle detection and classification system comprising:
   a sampling area including a fluid to be measured;
   a light source on a first side of said sampling area;
   a first detector on a second side of said sampling area;
   a second detector on a second side of said sampling area;
   a parabolic reflector having a vertex located on the first side of said sampling area and a focal point within said sampling area;
   wherein, said light source supplies substantially collimated light defining a first axis; and
   wherein said light source, said sampling area, said first detector and said second detector are located along said first axis;
   and further comprising a scattered light collection lens located along said first axis on a second side of said sampling area between said sampling area and said first detector, and a fluorescent light condenser lens located along said first axis on a second side of said sampling area between said sampling area and said second detector, wherein said scattered light collection lens defines an aperture about said first axis, and wherein said fluorescent light collection lens is located within said aperture.

* * * * *